(12) United States Patent
Liu

(10) Patent No.: US 9,101,729 B2
(45) Date of Patent: Aug. 11, 2015

(54) ELECTRONIC CIGARETTE AND INHALING SHELL THEREOF

(75) Inventor: Qiuming Liu, Shenzhen (CN)

(73) Assignee: HUIZOU KIMREE TECHNOLOGY CO., LTD., SHENZHEN BRANCH, Shenzhen, Guangdong (CN)

(*) Notice: Subject to any disclaimer, the term of this patent is extended or adjusted under 35 U.S.C. 154(b) by 330 days.

(21) Appl. No.: 13/581,318

(22) PCT Filed: Jun. 5, 2012

(86) PCT No.: PCT/CN2012/076492
§ 371 (c)(1),
(2), (4) Date: Aug. 26, 2012

(87) PCT Pub. No.: WO2013/181796
PCT Pub. Date: Dec. 12, 2013

(65) Prior Publication Data
US 2013/0319407 A1 Dec. 5, 2013

(51) Int. Cl.
*A61M 15/06* (2006.01)
*A24F 47/00* (2006.01)
*A61M 11/04* (2006.01)

(52) U.S. Cl.
CPC .............. *A61M 15/06* (2013.01); *A24F 47/008* (2013.01); *A61M 11/041* (2013.01); *A61M 11/042* (2014.02); *A61M 11/044* (2014.02); *A61M 2205/3653* (2013.01); *A61M 2205/8206* (2013.01)

(58) Field of Classification Search
CPC ....................................................... A61M 15/06

USPC ........... 128/202.21, 203.23, 203.27; 131/270, 131/273, 194
See application file for complete search history.

(56) References Cited

U.S. PATENT DOCUMENTS

| 8,528,569 B1* | 9/2013 | Newton .......................... 131/194 |
| 8,857,446 B2* | 10/2014 | Wu ................................. 131/273 |
| 8,863,752 B2* | 10/2014 | Hon ................................ 131/194 |
| 2011/0011396 A1* | 1/2011 | Fang ......................... 128/202.21 |
| 2011/0036346 A1* | 2/2011 | Cohen et al. .............. 128/200.14 |
| 2011/0277756 A1* | 11/2011 | Terry et al. ................ 128/202.21 |
| 2011/0303231 A1* | 12/2011 | Li et al. .......................... 131/329 |

* cited by examiner

*Primary Examiner* — Justine Yu
*Assistant Examiner* — Kathrynn Reilly
(74) *Attorney, Agent, or Firm* — Cheng-Ju Chiang

(57) ABSTRACT

An electronic cigarette and an inhaling shell are disclosed. A mouthpiece is disposed at one end of an inhaling tube, a tobacco-liquid cup and atomizing device are disposed in the inhaling tube. The atomizing device includes an atomizing cup and an atomizer. The atomizer includes an electric heat wire and a fiber piece. The atomizing cup includes a cup seat, a cup cylinder, a support tube fixed on the cup seat and a liquid-storage member fitted around the support tube. The fiber piece is fixed on the support tube with both ends against an inner wall of the liquid-storage member to absorb tobacco liquid for atomization. The electronic cigarette and the atomizing device of the present invention facilitate disassembly and assembly, maintenance, and replacement, facilitate repeatedly adding tobacco liquid into the tobacco-liquid cup, and simplify manufacturing the electronic cigarette. The configuration of an air-puffing passage thereof makes the inhaling shell more compact.

20 Claims, 11 Drawing Sheets

ELECTRONIC CIGARETTE AND INHALING SHELL THEREOF

CROSS REFERENCE TO RELATED APPLICATIONS

The present application is a 35 U.S.C. §371 National Phase conversion of International (PCT) Patent Application No. PCT/CN2012/076492, filed on Jun. 5, 2012, the disclosure of which is incorporated by reference herein. The PCT International Patent Application was filed in Chinese.

FIELD OF THE INVENTION

The present invention relates to an electronic cigarette, and especially to an electronic cigarette and an inhaling shell thereof which can be repeatedly added with tobacco liquid repeatedly and can be replaced with an atomizing device thereof.

BACKGROUND OF THE INVENTION

An inhaling shell of an existing electronic cigarette includes a non-transparent inhaling tube, an atomizing device disposed in the inhaling tube which includes electric heat wire and atomizing cup, a tobacco-liquid cup disposed in the inhaling tube for storing tobacco liquid, an elongated liquid-guide tube for guiding tobacco liquid to flow into the atomizing device, a mouthpiece disposed at one end of the inhaling tube, an air-puffing passage for transporting aerosol to outside of the inhaling tube which is generated from tobacco-liquid vaporization by atomizing device. The air-puffing passage is configured in the inhaling tube and molded with the inhaling tube by an integrated molding process. Both ends of the electric heat wire are soldered to first and second electrodes by a wire-bond process or a copper-tube riveting process.

The inhaling shell of the existing electronic cigarette has such disadvantages that: the atomizing device is single use only and it is inconvenient to repeatedly add tobacco liquid into the tobacco-liquid cup; the atomizing device and the tobacco-liquid cup are fixed in the inhaling tube and non-replaceable; the electric heat wire of the atomizing device is connected to electric circuit by wire-bond process or copper-tube riveting process, which process is very complicated and inconvenient for installation; additionally, liquid-guide tube extends into the tobacco-liquid cup, which is complicated and inconvenient for installation, and results in fluid leaking and bad results of guiding tobacco liquid; moreover, the air-puffing passage is configured and integrated in the inhaling tube, it is necessary to specially preset space for the air-puffing passage, and thus results in an incompact inner structure or a bigger dimension of the inhaling tube; and for the opaque inhaling tube, tobacco-liquid volume in the tobacco-liquid cup is unobservable, thus unfavorable-smell gas generated from burning electric heat wire will be inhaled after the tobacco liquid is exhausted.

SUMMARY OF THE INVENTION

A main object of the present invention is to provide an inhaling shell of an electronic cigarette, which is convenient for disassembly and assembly, maintenance, and replacement of an atomizing device; and is convenient to repeatedly add tobacco liquid into an atomizing cup thereof, simplifies manufacturing of the inhaling shell, improves performances of guiding and sealing tobacco liquid, facilitates assembly and use of the inhaling shell, supplies an air-puffing passage ensuring the inhaling shell more compact; and has good heat insulation; and in which tobacco liquid amount is observable.

To obtain the above object, an inhaling shell of the present invention comprises a mouthpiece, an inhaling tube, a tobacco-liquid cup, an atomizing device. The mouthpiece is disposed at one end of the inhaling tube. The tobacco-liquid cup and the atomizing device are disposed in the inhaling tube. The atomizing device comprises an atomizing cup and an atomizer. The atomizing cup defines an atomizing chamber for receiving the atomizer and defines an air hole communicating the atomizing chamber. The atomizer comprises electric heat wire and a fiber piece for supporting the electric heat wire and absorbing tobacco liquid. The atomizing cup comprises a cup seat, a cup cover and a cup cylinder resting on the cup seat. Within the atomizing cup, therein are a support tube and a liquid-storage member mounted on the cup seat. The liquid-storage member is fitted around the support tube. The fiber piece is fixed on the support tube, and both ends of the fiber piece respectively abut against inner wall of the liquid-storage member and absorb tobacco liquid for atomization by the electric heat wire.

Furthermore, the tobacco-liquid cup has one end open to form a tobacco-liquid output port. The cup cover has a duct fitted into the tobacco-liquid output port. The atomizing device further comprises a liquid-guide piece inserted in the cup cover and in the duct thereof. The liquid-guide piece has one end extending into the tobacco-liquid cup, and the other end extending to the atomizing cup and abutting against the liquid-storage member so as to guide the tobacco liquid into the atomizing cup.

Furthermore, the tobacco-liquid cup has the other end forming a tobacco-liquid input port. The mouthpiece comprises a main body with an airflow hole defined therein and a plug engaged with the tobacco-liquid input port of the tobacco-liquid cup. The plug removably seals the tobacco-liquid input port so as to repeatedly add tobacco liquid.

Furthermore, the air hole and atomizing chamber of the atomizing cup, an air outlet defined in the cup cover and communicating the atomizing chamber, a vent groove defined along outer wall of the tobacco-liquid cup with one end thereof communicating the air outlet of the cup cover and the other end communicated the environment through the airflow hole of the mouthpiece, all together construct an air-puffing passage for vapor mist from tobacco liquid vaporized by the atomizer to pass therethrough to the mouthpiece for smoking.

Furthermore, the inhaling tube is installed with a thermal insulation jacket therein for heat insulation. The thermal insulation jacket is disposed between an inner wall of the inhaling tube and the tobacco-liquid cup; and the tobacco-liquid cup and the atomizing device is accommodated in the thermal insulation jacket.

Furthermore, the inhaling tube is installed with a mounting sleeve for mounting the tobacco-liquid cup and receiving the atomizing device. Bottom end of the thermal insulation jacket abuts against the mounting sleeve, and both are further engaged with each other via a snap-fit mechanism. The mounting sleeve abuts against the cup cover and both are electrically connected.

Furthermore, an electrode member of the atomizing device is inserted in the cup seat and both together define the air hole of the atomizing cup. The electric heat wire has one end thereof tightly fitted on an outer wall of the electrode member for electric connection, and has the other end tightly fitted on an inner wall of the cup cylinder for electric connection; and the cup cylinder and cup cover are electrically connected with each other.

Furthermore, the inhaling tube at the other end opposite to the mouthpiece is installed with a joint member for mounting the atomizing device in the mounting sleeve. The joint member and the mounting sleeve are moveably engaged and electrically connected with each other. An electrode piece with a center through-hole is fixed in the joint member by an insulating ring, and electrically contacts an end of the electrode member of the atomizing device which is inserted in the cup seat, the center through-hole communicates the air hole of the atomizing cup; the electrode piece in the joint member in a sidewall thereof defines an air vent which communicates the center through-hole.

Furthermore, the cup cylinder, the liquid-storage member, and the support tube are shaped about as a cylinder and coaxially arranged; the liquid-storage member in an inner wall thereof is further installed with a liquid-soakage member which has a cylindrical shape and a high-temperature resistance, and the liquid-soakage member is fitted outside of the support tube; both ends of the fiber piece abut against an inner wall of the liquid-soakage member; tobacco liquid into the atomizing chamber from the liquid-guide piece is absorbed and stored in the liquid-storage member, penetrates the liquid-soakage member, and is sucked into the fiber piece for atomization; the support tube at a top end thereof defines fix openings which radially penetrate through a wall of the support tube and are used for supporting the fiber piece; inside of the cup seat is set with a positioning column for locating the support tube, the positioning column axially projects upwards to a certain height from a bottom center of the cup seat; the air hole of the atomizing cup axially runs through the positioning column and the bottom of the cup seat; and the bottom of the cup seat further defines a wire-through hole for the electric heat wire passing therethrough.

Furthermore, the liquid-storage member is made from liquid-absorbing cotton or fiber; the liquid-soakage member is made from high-temperature resistant cotton or fiber; and the support tube is made from glass fiber.

Furthermore, the liquid-guide piece is a kind of cotton or fiber which can absorb tobacco liquid, comprises an effusion end in an extratensive-speaker shape and contacting with top surface of the liquid-storage member.

Furthermore, the main body of the mouthpiece is shaped about as a cylinder, the plug as a sealing plug is made from elastic materials; a sealing gasket is disposed where the plug and the tobacco-liquid input port are engaged; and the airflow hole of the main body comprises an axial hole intercommunicated with a radial hole.

Furthermore, the inhaling tube is a tapered cylinder with decrescent diameter.

Furthermore, the inhaling tube is set with an observation window for observing tobacco-liquid volume in the tobacco-liquid cup, and the tobacco-liquid cup is wholly or partly transparent; the inhaling tube is fitted with a decoration sheath for decoration or bearing a log.

To obtain the above object, an electronic cigarette in the present invention is proposed to comprise the inhaling shell described above, and a power shell connecting with the inhaling shell.

Since the atomizing device comprises cup cover, cup cylinder and cup seat, which together defines the atomizing chamber; the atomizing cup further comprises the liquid-storage member inserted in the cup cylinder, the liquid-soakage member inserted in the liquid-storage member, and the support tube inserted in the liquid-soakage member; such structure brings that tobacco liquid is prestored in the liquid-storage member after being guided into the atomizing chamber by the liquid-guide piece, and penetrates from the liquid-storage member through the liquid-soakage member to the atomizing chamber for atomization, such atomizing device facilitates assembly, maintenance, and displacement of the same, and has good performance of guiding tobacco liquid and leakage-proof of tobacco liquid.

The mouthpiece is removably set to the inhaling tube, which achieves tight fit with the tobacco-liquid cup and refilling tobacco liquid into the tobacco-liquid cup; in which tobacco liquid can be repeatedly added; and the use is convenient.

The atomizing device is detachably installed in the mounting sleeve by means of the joint member, which facilitates assembly and disassembly, maintenance, and replacement.

Additionally, it is not necessary to specially design or preserve a structure space for an air-puffing passage, which make an inner structure of the inhaling shell more impact.

Moreover, both ends of the electric heat wire are respectively fitted with a first and a second electrode of the atomizing device, soldering is not necessary, which simplifies process and facilitates assembly.

Furthermore, the inhaling tube is set with an observation window, the thermal insulation jacket, and the tobacco-liquid cup is transparent or semitransparent, which is convenient to observe tobacco liquid volume in the tobacco-liquid cup, and avoid burning the electric heat wire after tobacco liquid is exhausted; and the thermal insulation jacket give a good heat insulation when the inhaling shell of the electronic cigarette is in use.

finally, outer wall of the inhaling tube is fitted with the decoration sheath, thus a log can be adhered thereon.

An embodiment of the present invention taken in conjunction with the accompanying drawings is described in detail as follows.

DETAILED DESCRIPTION OF THE INVENTION

As shown in FIG. 1 to FIG. 13, a first embodiment of the present invention provides an electronic cigarette. The electronic cigarette comprises an inhaling shell 90 and a power shell 91. Herein a connecting means between the inhaling shell 90 and the power shell 91 of the electronic cigarette maybe fitting connection, plug connection, or threaded connection. The threaded connection is used in this embodiment.

Figure 1:
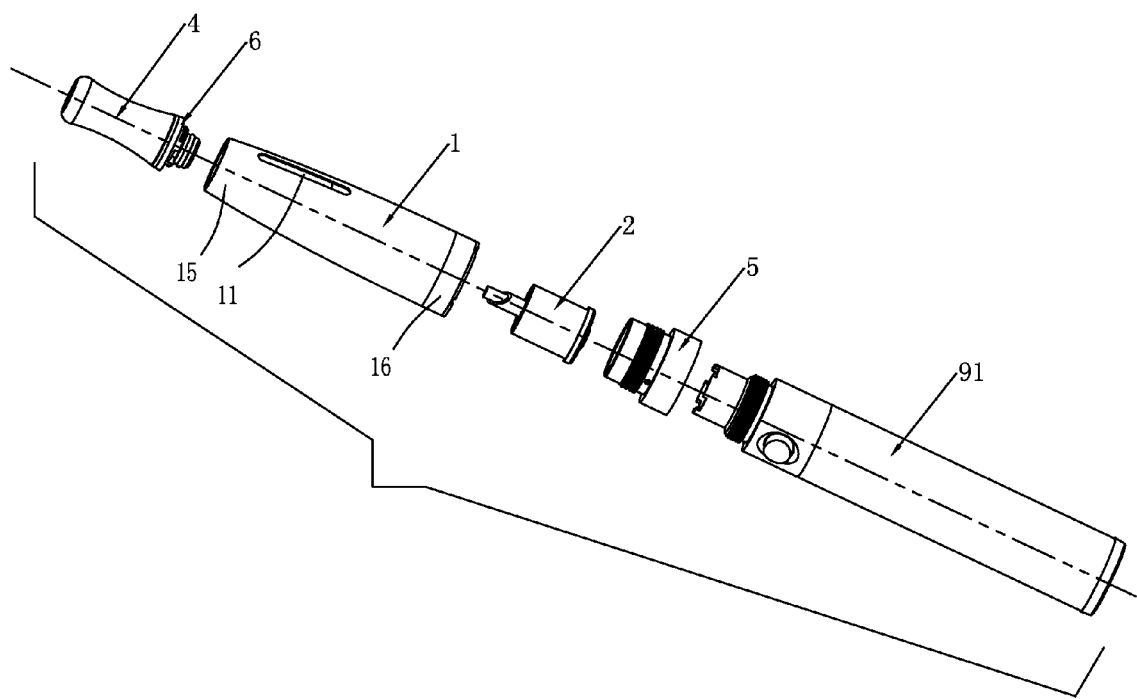
FIG. 1 is an exploded, perspective view of an electronic cigarette in accordance with an embodiment of the invention.
Figure 2:
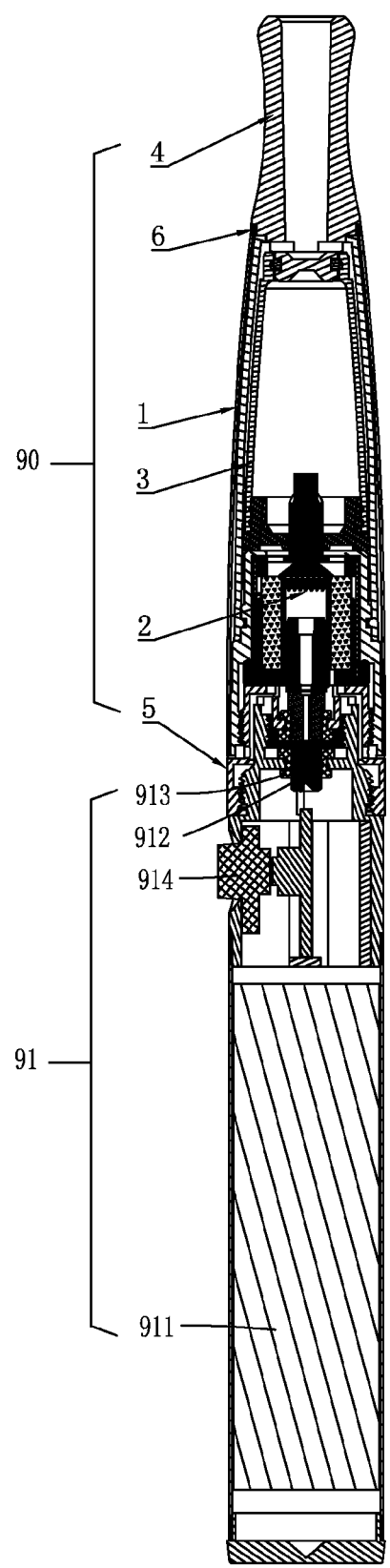
FIG. 2 is a cross-sectional view of the electronic cigarette in accordance with the embodiment of the invention.
Figure 3:
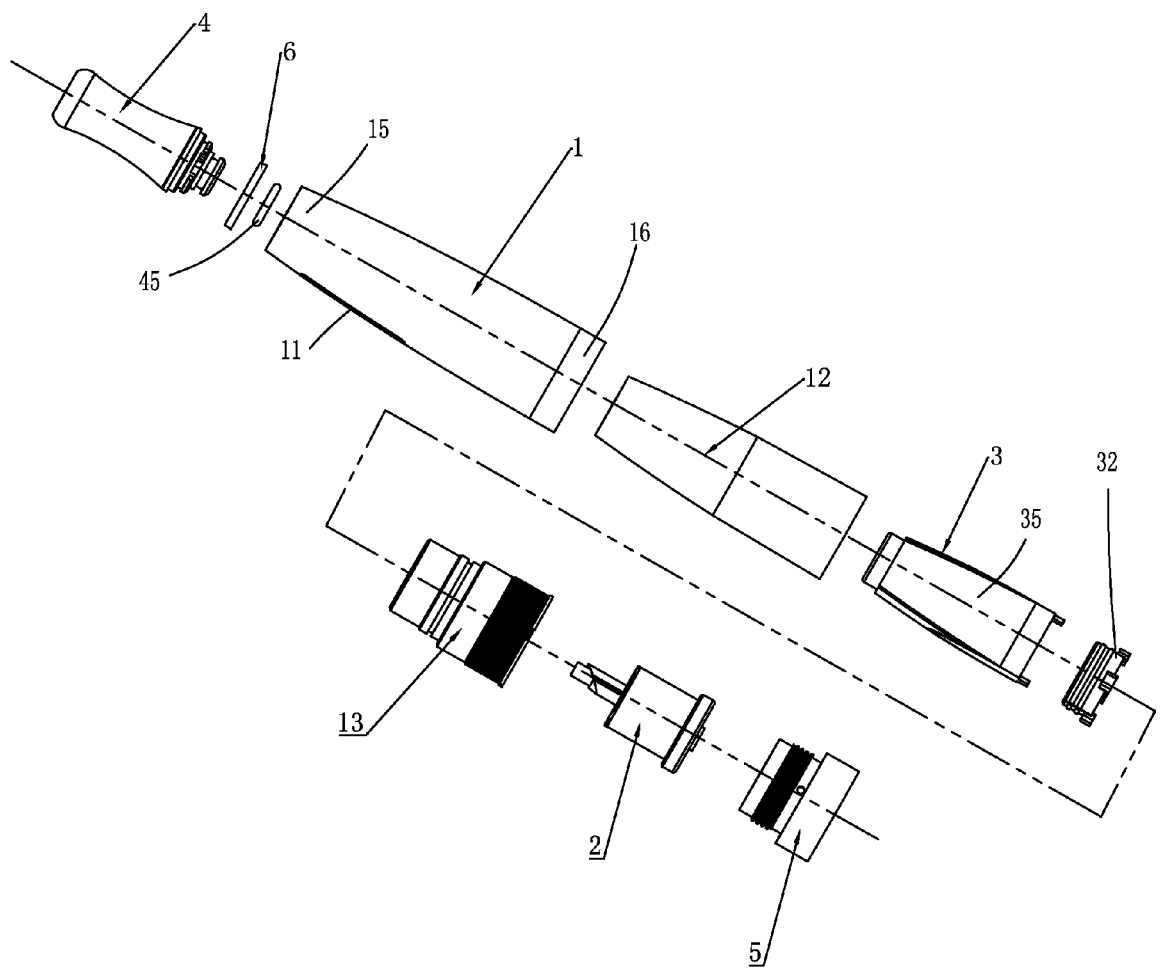
FIG. 3 is an exploded, perspective view of an inhaling shell of the electronic cigarette in accordance with the embodiment of the invention.
Figure 4:
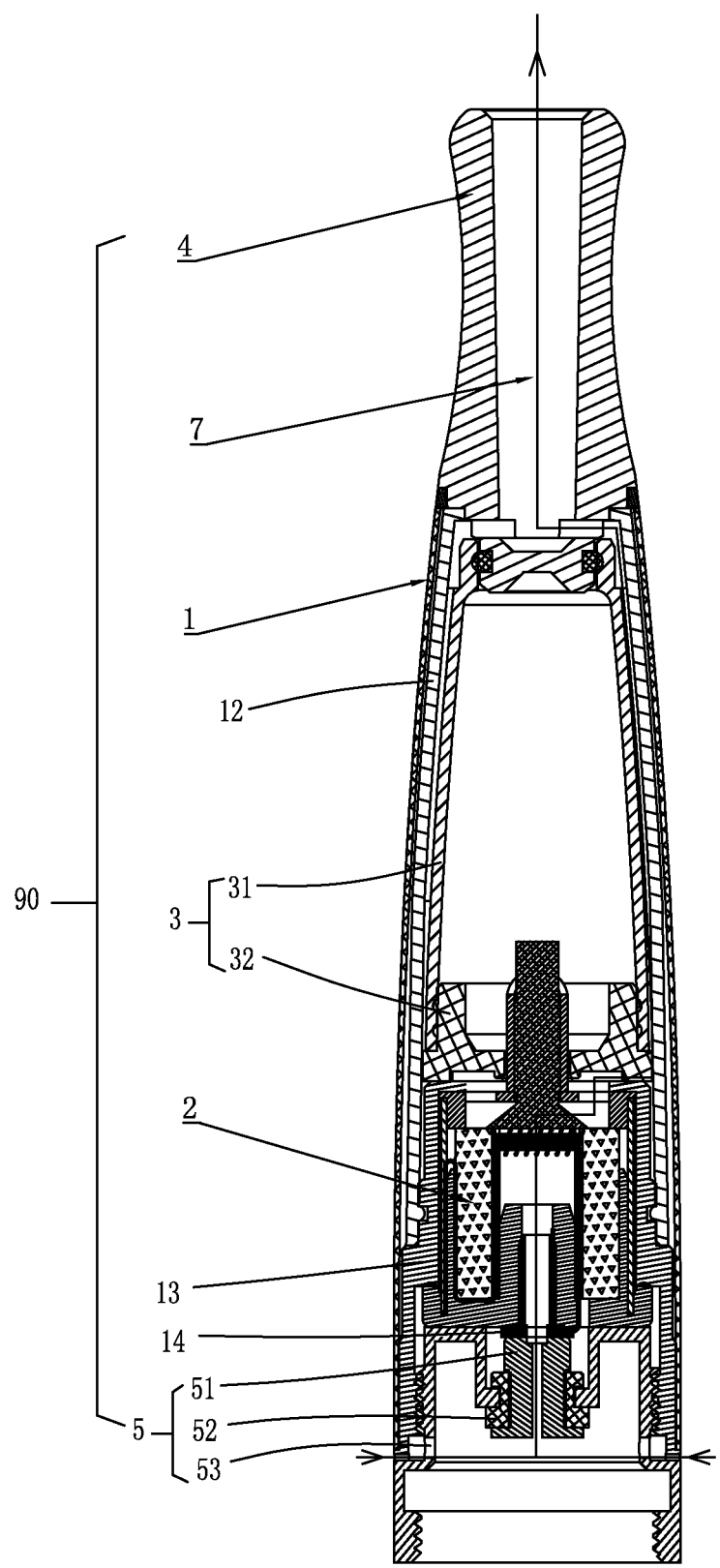
FIG. 4 is a cross-sectional view of the inhaling shell in accordance with the embodiment of the invention.

As shown in FIG. 3-4, the inhaling shell 90 comprises an inhaling tube 1, an atomizing device 2, a tobacco-liquid cup 3, a mouthpiece 4, a joint member 5, and an air-puffing passage 7. The inhaling tube 1 therein is installed with the tobacco-liquid cup 3 for containing tobacco liquid, and the atomizing device 2 adjacent to the tobacco-liquid cup 3 for vaporizing tobacco liquid into aerosol. One end of the inhaling tube 1 is set with the mouthpiece 4, and the other end is set with the joint member 5 for connecting with the power shell 91. The atomizing device 2 is mounted in the inhaling shell 1 in virtue of the joint member 5, and the air-puffing passage 7 is defined inside the inhaling shell 90 of the electronic cigarette for air and vapor mist flowing therethrough.

The inhaling tube 1 is a hollow and long cylinder. In this embodiment, it is shaped as about a cylindrical housing with diameters thereof gradually decreased towards the mouthpiece 4, namely, the inhaling tube 1 is a tube with a preset taper. Certainly, other shapes are also applicable. It is made from stainless steel, and may be made from plastic or other applicable material as well. The inhaling tube 1 is wholly transparent or at least partly transparent, and it is transparent where the tobacco-liquid cup 3 is located so as to observe tobacco-liquid volume in the tobacco-liquid cup 3. Specifically, the inhaling tube 1 maybe set with an observation window 11 for observing tobacco liquid in the tobacco-liquid cup 3. The inhaling tube 1 therein is further set with a thermal insulation jacket 12 for heating insulation, a mounting sleeve 13 also used as a second electrode (such as negative electrode) of the atomizing device 2, and an electrode member 14 as a first electrode (such as positive electrode) of the atomizing device 2. The inhaling tube 1 with both ends open, comprises a top section 15 engaged with the mouthpiece 4 and a bottom section 16 engaged with the power shell 91. The top section 15 has a corresponding top-end flange thereof extending inwards to form a first circular lip for fitting the mouthpiece 4.

Figure 5:
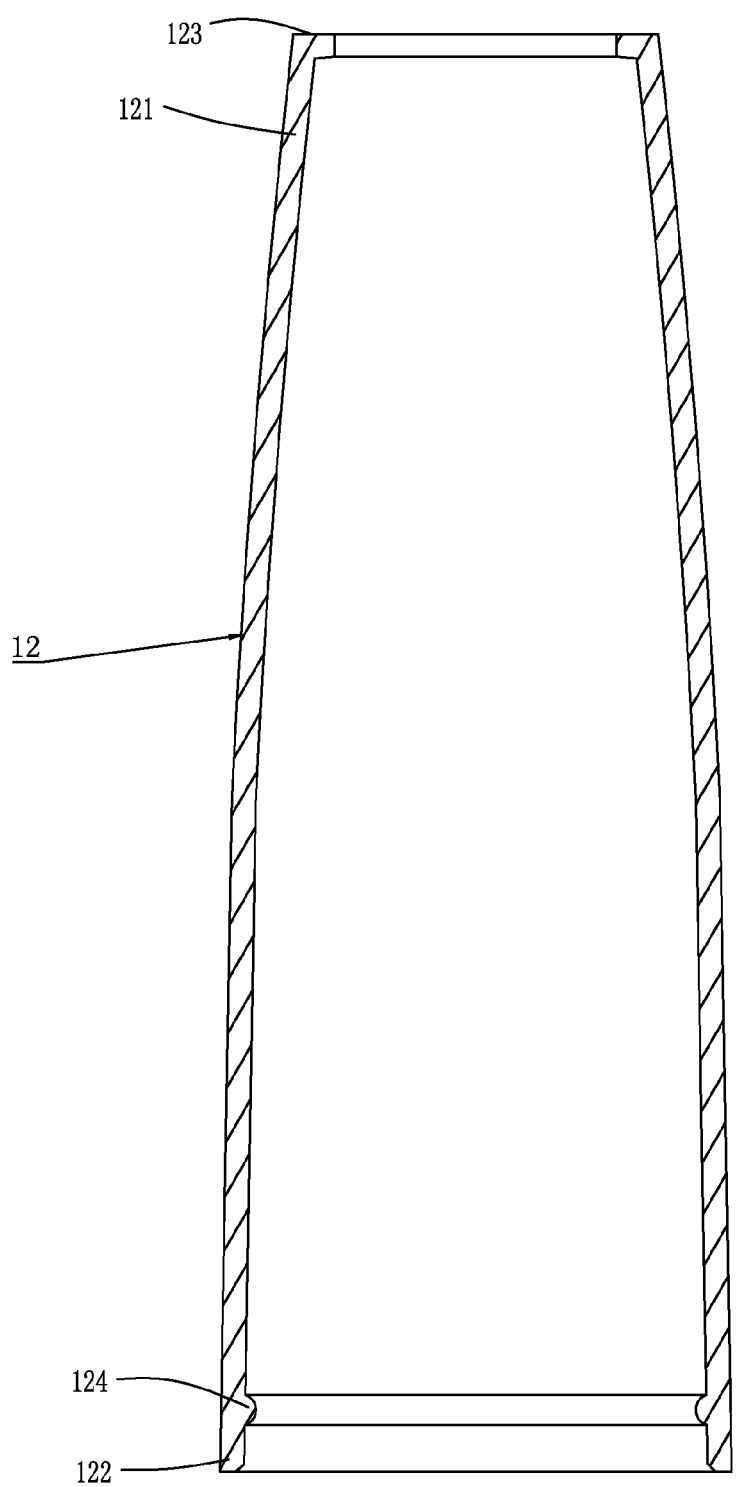
FIG. 5 is a cross-sectional view of a thermal insulation jacket of the inhaling shell in accordance with the embodiment of the invention.

The thermal insulation jacket 12 (as shown in FIG. 5) is disposed in the inhaling tube 1. The thermal insulation jacket 12 has a hollow-cylinder structure, and has a shape adapted to the inhaling tube 1. In this embodiment, the thermal insulation jacket 12 is a long cylinder in a preset taper degree and with both ends open. The thermal insulation jacket 12 comprises a top section 121 and a bottom section 122, a corresponding top end of the top section 121 forms a second circular lip 123 which abuts against interior of the first circular lip of the inhaling tube 1 at the top end thereof so as to further fit the mouthpiece 4, while an inner wall of the bottom section 122 forms a flange 124. The thermal insulation jacket 12 may be made from silica gel with better heat resistance so as to obtain good heat insulation, and in use, a temperature of an outer wall of the inhaling shell 90 keeps relatively low, which is not hot for hand or mouth. Other heat insulating materials are applicable as well.

Figure 6:
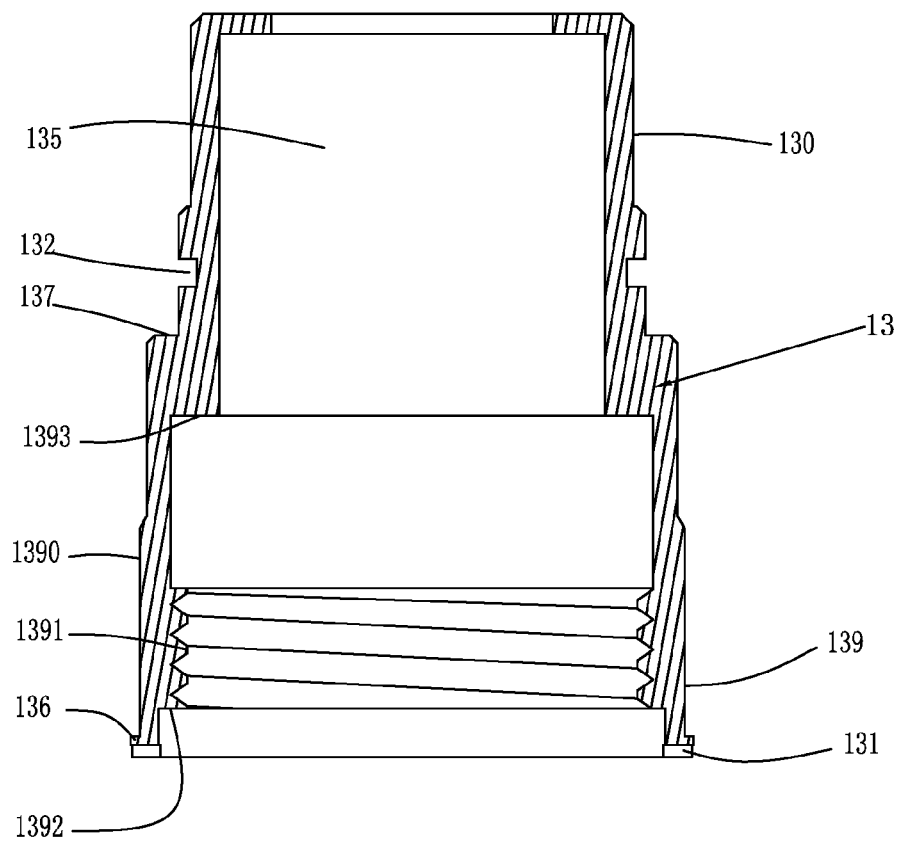
FIG. 6 is a cross-sectional view of a mounting sleeve of the inhaling shell in accordance with the embodiment of the invention.
Figure 7:
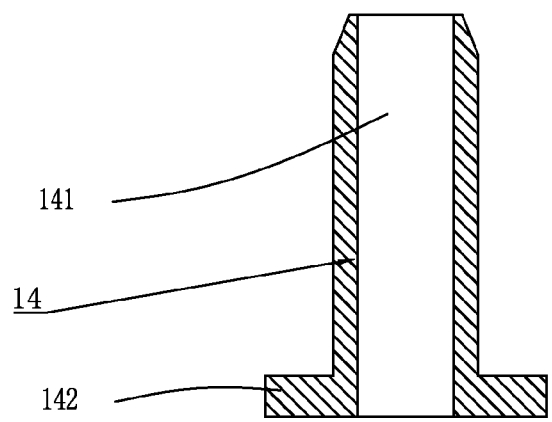
FIG. 7 is a cross-sectional view of an electrode member of the inhaling shell in accordance with the embodiment of the invention.

The mounting sleeve 13 (as shown in FIGS. 3, 4, and 6) is disposed in the bottom section 16 of the inhaling tube 1, is used for mounting the tobacco-liquid cup 3 in the inhaling tube 1, and also used for receiving the atomizing device 2. In this embodiment, the mounting sleeve 13 is further used as the second electrode of the atomizing device 2, and made from metal of electric-conduction material, such as cupper. The mounting sleeve 13 has a shape adapted to the inhaling tube 1. In this embodiment, the mounting sleeve 13 is shaped about as a hollow cylinder with both ends open, and comprises an upper section 130 with a relatively smaller diameter and a lower section 139 with a relatively bigger diameter. The upper section 130 has its top-end flange radially extending inwards to form a third lip; the lower section 139 has its sidewall at a bottom end thereof radially defining an air inlet 131 so that outer air can flow into the inhaling tube 1, and the bottom end of the lower section 139 radially extends outwards to form a first positioning step 136 for bearing the bottom end of the inhaling tube 1. The upper section 130 defines a receiving chamber 135 therein for receiving the atomizing device 2; its outer wall forms a fit groove 132 engaged with the flange 124 of the thermal insulation jacket 12, and forms a second positioning step 137 for bearing the bottom end of the thermal insulation jacket 12; and the upper section 130 of the mounting sleeve 13 is inserted in the thermal insulation jacket 12. The lower section 139 has its outer wall forming raised pattern 1390 used for tightly fitted in the inhaling tube 1, while has its inner wall forming internal thread 1391 used for threadedly engaged with the joint member 5, has its inner wall at its bottom end forming a first innerstep 1392 and far from the bottom end forms a second innerstep 1393. The mounting sleeve 13 is electrically connected with a second electrode in the power shell 91 via being threadedly engaged with the joint member 5.

It is understood that, a snap-fit mechanism between the thermal insulation jacket 12 and the mounting sleeve 13 is performed by the flange 124 being fitted in the fit groove 132, while instead, the flange 124 may be set on an outer wall of the mounting sleeve 13, and the fit groove 132 may be set in the inner wall of the thermal insulation jacket 12. Additionally, the second circular lip 123 at a top end of the thermal insulation jacket 12 abuts against the first circular lip at a top end of the inhaling tube 1, the bottom end 122 of the thermal insulation jacket 12 abuts against the step 137 formed on the outer wall of the upper section 130 of the mounting sleeve 13, thereby the thermal insulation jacket 12 is mounted in the inhaling tube 1. The mounting sleeve 13 is inserted in the inhaling tube 1 in such a manner that the bottom end of the inhaling tube 1 abuts against the first positioning step 136 of the bottom section 139 of the mounting sleeve 13. Such configurations make assembly of the inhaling shell 90 simple and its structure more secure.

The electrode member 14 is fixed in the atomizing device 2, and electrically connected with conductive parts of the atomizing device 2. In this embodiment, the electrode member 14 is used as the first electrode. The electrode member 14 is shaped as a cylinder, defines a venthole 141 axially running through center of the electrode member 14, and bottom end of the electrode member 14 radially extends outwards to form a flange 142.

Figure 8:
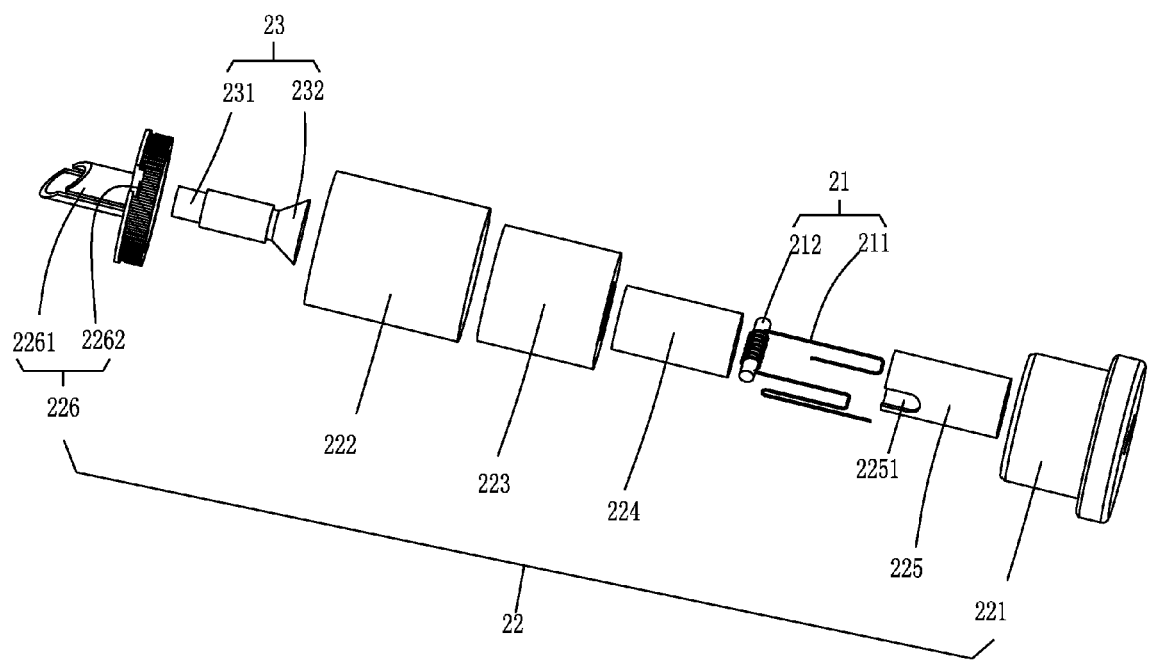
FIG. 8 is an exploded, perspective view of an atomizing device of the inhaling shell in accordance with the embodiment of the invention.
Figure 9:
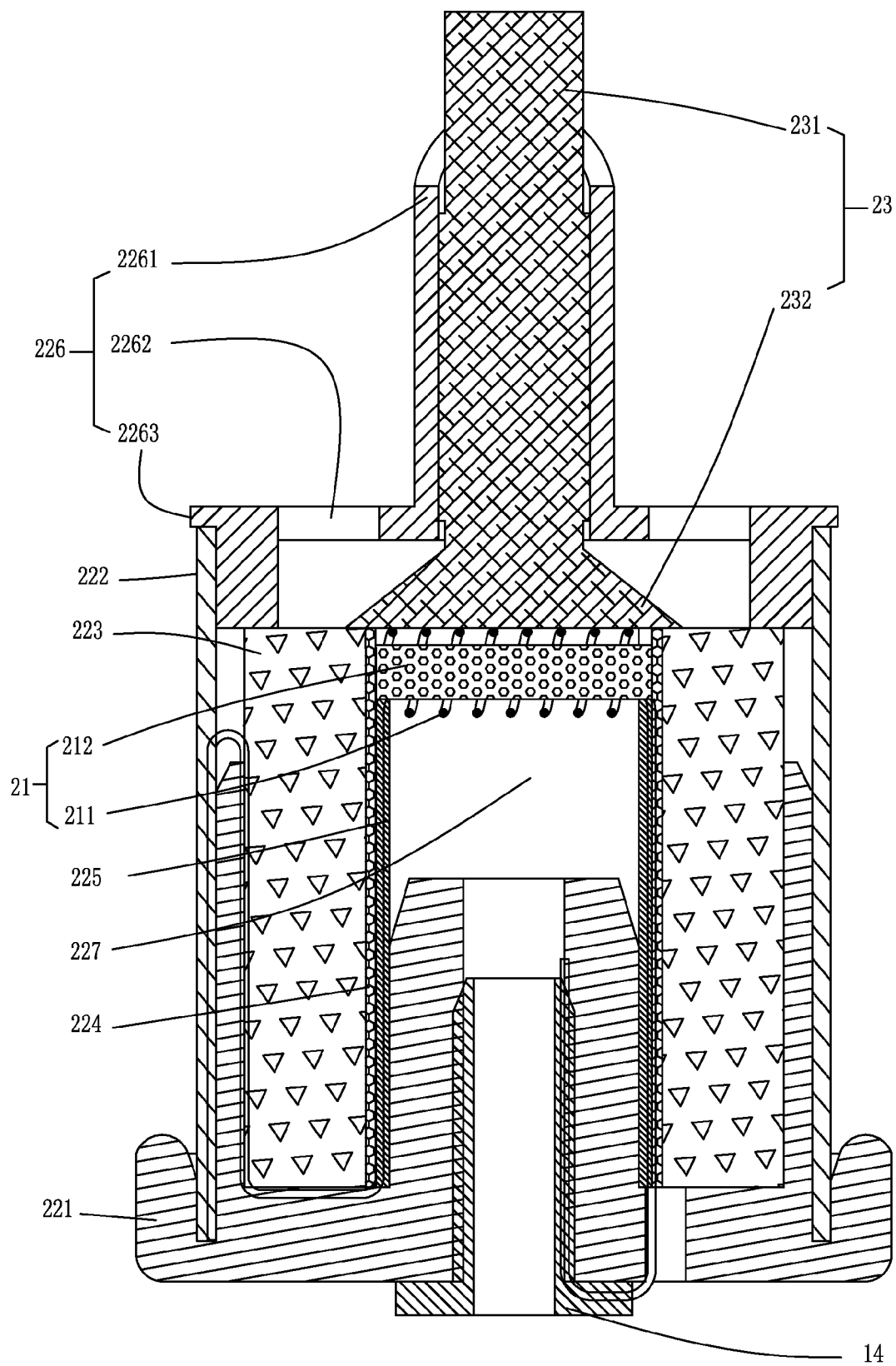
FIG. 9 is a cross-sectional view of the atomizing device of the inhaling shell in accordance with the embodiment of the invention.
Figure 10:
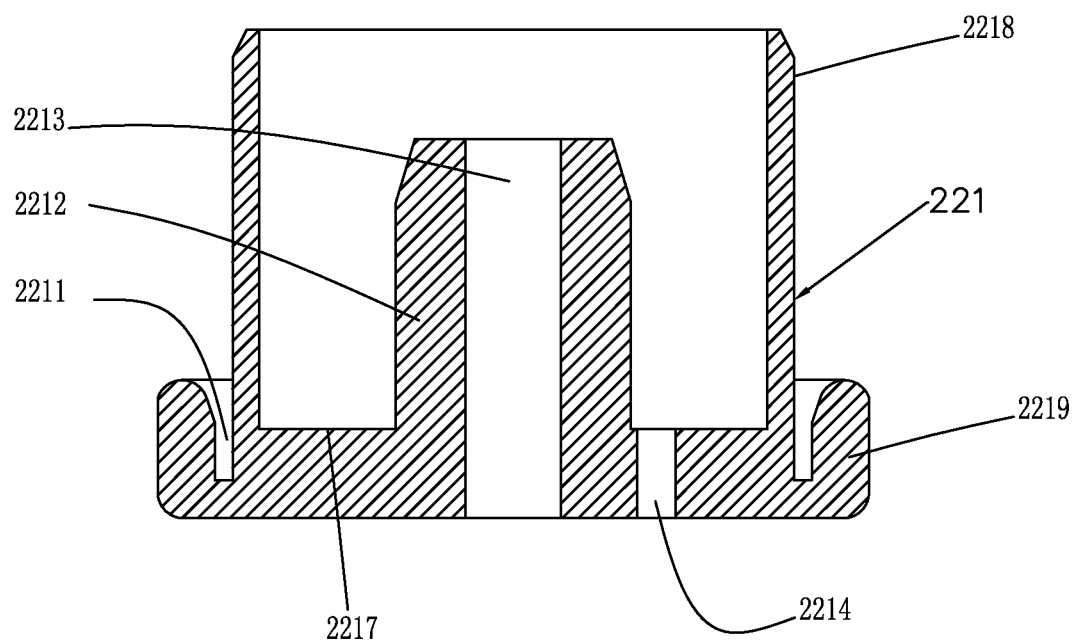
FIG. 10 is a cross-sectional view of a cup seat of the atomizing device in accordance with the embodiment of the invention.
Figure 11:
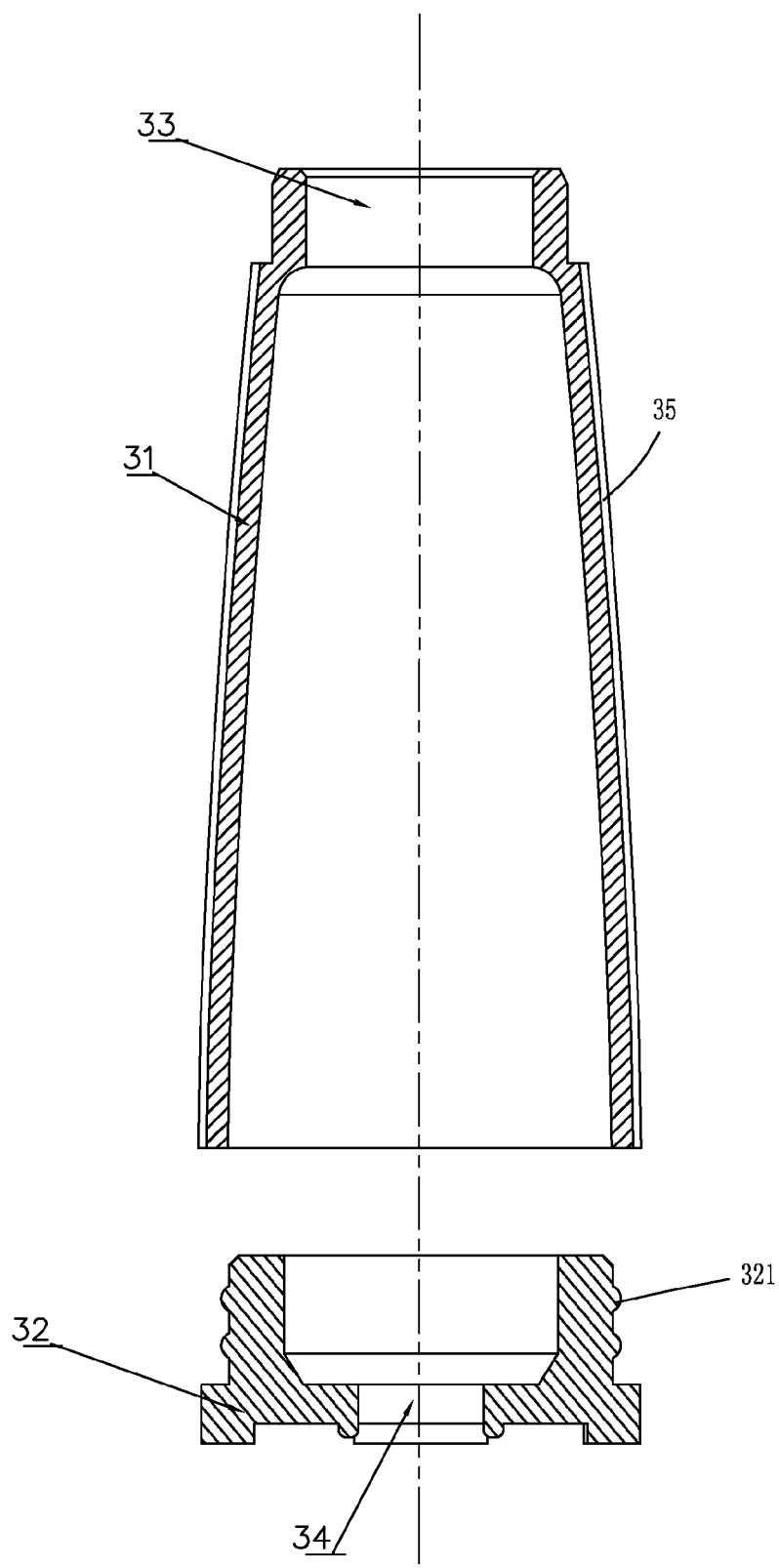
FIG. 11 is an exploded, cross-sectional view of a tobacco-liquid cup of the inhaling shell in accordance with the embodiment of the invention.
Figure 12:
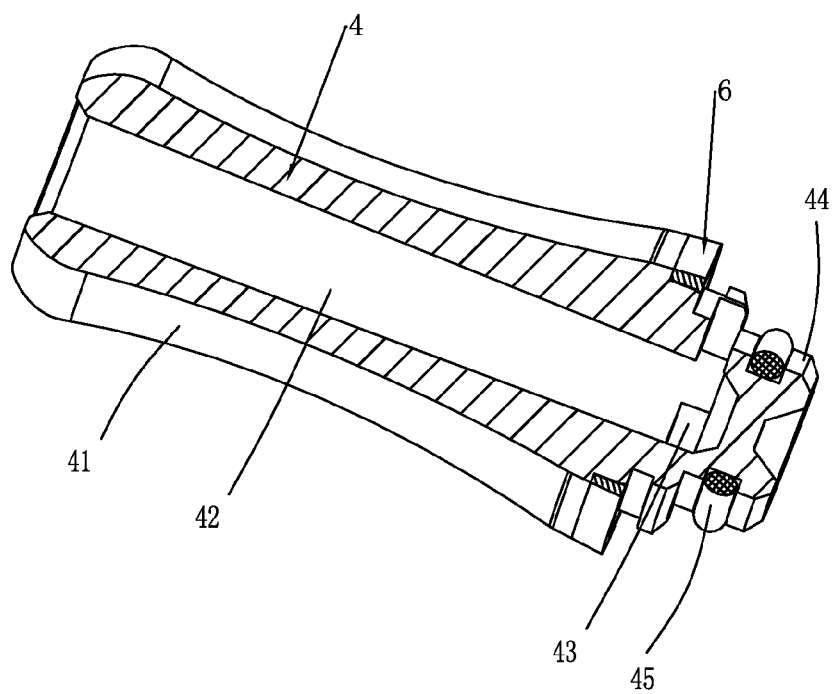
FIG. 12 is a cross-sectional view of a mouthpiece of the inhaling shell in accordance with the embodiment of the invention.
Figure 13:
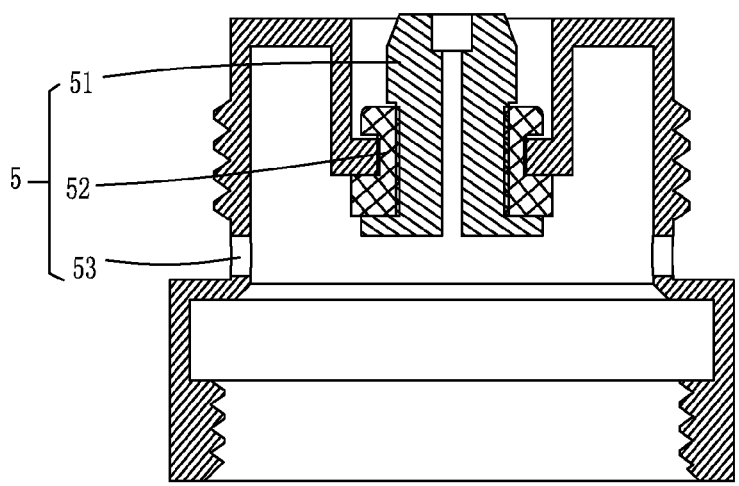
FIG. 13 is a cross-sectional view of a joint member of the inhaling shell in accordance with the embodiment of the invention.

The atomizing device 2 (as shown in FIGS. 8-10) comprises an atomizer 21, an atomizing cup 22 and a tobacco-liquid guide piece 23, namely a liquid-guide piece 23.

The atomizer 21 is used for vaporizing tobacco liquid into aerosol mist, and comprises an electric heat wire 211 and a fiber piece 212; the electric heat wire 211 winds around the fiber piece 212, and is held and fixed in the atomizing cup 22 by virtue of the fiber piece 212. The fiber piece 212 is used to absorb tobacco liquid for the electric heat wire 211 to heat tobacco liquid into vapor, and the fiber piece 212 may be shaped as a cylinder.

The atomizing cup 22 comprises a cup seat 221, a cup cylinder 222, a liquid-storage member 223, a liquid-soakage member 224, a support tube 225, and a cup cover 226. The cup cylinder 222, the liquid-storage member 223, the liquid-soakage member 224 and the support tube 225 are shaped about as a cylinder and coaxially arranged.

The cup seat 221 (as shown in FIG. 10) may be made from plastic material, comprises a circular bottom 2217, a sidewall 2218, and a periphery of the bottom 2217 forms a cup flange 2219. A groove 2211 is defined between the cup flange 2219 and the sidewall 2218 for fixing the cup cylinder 222. The cup flange 2219 has its top end abutting against the second inner-step 1393 of the mounting sleeve 13 and has its bottom end abutting against the joint member 5 (as shown in FIG. 4), so that the atomizing cup 22 is fixed in the mounting sleeve 13. The cup seat 221 therein is further set with a positioning column 2212 for locating the supporting tube 225, and the positioning column 2212 axially and upwards extends from a center of the bottom 2217 to a certain height. An air hole 2213 axially runs through the positioning column 2212 and the bottom 2217. The bottom 2217 further defines a wire-through hole 2214 for the electric heat wire 211 running therethrough. The electrode member 14 is inserted into the air hole 2213 of the atomizing cup 22 from the bottom 2217, and a circuit is electrically connected in such way that the flange 142 of the electrode member 14 exposing out of the cup seat 221 contacts a corresponding part of the joint member 5.

The cup cylinder 222 has a hollow-shell structure, fits around outside of the sidewall 2218 of the cup seat 221, has its bottom end fixed in the groove 2211, and is made from metallic conductive material, such as cupper, so as to electrically connect with the electric heat wire 211 and the mounting sleeve 13.

The liquid-storage member 223 absorbs and stores tobacco liquid in the atomizing cup 22 from the liquid-guide piece 23 for the atomizer 21 vaporizing tobacco liquid, is inserted in the cup cylinder 222, and also has a hollow-cylinder structure. The liquid-soakage member 224 has a hollow-cylinder structure as well, is tightly fitted in inner wall of the liquid-storage member 223 so as to absorb tobacco liquid from the liquid-storage member 223. The liquid-storage member 223 and the liquid-soakage member 224 are tobacco-liquid reservoirs which can absorb and store liquid like a sponge, the liquid-storage member 223 is made from cotton or fiber which can absorb liquid; and the liquid-soakage member 224 is made from high-temperature resistant cotton or fiber.

The support tube 225 also has a hollow-cylinder structure, is inserted between the positioning column 2212 of the cup seat 221 and the liquid-soakage member 224 so as to fix the liquid-storage member 223 and the liquid-soakage member 224 between the sidewall 2218 and the positioning column 2212 of the cup seat 221, and acts as a support frame. The support tube 225 is made from glass fiber, and at its upper sidewall defines fix openings 2251 radially through the sidewall, which are used for holding the fiber piece 212 of the atomizer 21. The fiber piece 212 is mounted in the fix openings 2251; both ends of the fiber piece 212 respectively extend out of the support tube 225 from the fix openings 2251, abut against an inner wall of the liquid-soakage member 224, and absorb tobacco liquid therein for vaporization by heat.

The cup cover 226 is used for fixing the liquid-guide piece 23, and fits on the other end of the cup cylinder 222 opposite to the cup seat 221. The cup cover 226 is also a metal piece so as to electrically connect with the mounting sleeve 13, and the cup cover 226 electrically connects with the mounting sleeve 13 in such way that an upper edge of the cup cover 226 contacts the mounting sleeve 13. The cup cover 226 at its top surface axially forms a duct 2261 for fixing the liquid-guide piece 23, the liquid-guide piece 23 is inserted through the duct 2261, and the duct 2261 substantially is a tip tube with a relatively smaller inner diameter and extending to a preset height from the top surface of the cup cover 226. The duct 2261 and the cup cover 226 are hollow and communicated with each other, and the duct 2261 at one end far from the cup cover 226 has a tip top which leads the liquid-guide piece 23 therein smoothly extending into the tobacco-liquid cup 3. The cup cover 226 is further defined an air outlet 2262 of the atomizing cup 22 for emitting aerosol to outside of the atomizing cup 22, and radially extends outwards to form a flange 2263 which abuts against a top end of the cup cylinder 222.

In accordance with this embodiment, an atomizing chamber 227 as a hollow cavity is defined by the cup seat 221, the cup cylinder 222, and the cup cover 226 together. The fiber piece 212 of the atomizer 21 is mounted in the atomizing chamber 227 with an axial positioning by virtue of the liquid-storage member 224, and a radial positioning by virtue of both the liquid-guide piece 23 and the fix opening 2251 of the support tube 225. When the liquid-storage member 223, liquid-soakage member 224 and the support tube 225 are mounted in the atomizing chamber 227, a top surface of the liquid-storage member 223 abuts against a lower edge of the cup cover 226 to axially fix the liquid-storage member 224; a top end of the liquid-storage member 223 is higher than or equal to that of the liquid-soakage member 224, a top end of the support tube 225 is lower than that of the liquid-soakage member 224, and a top end of the positioning column 2212 is lower that of the support tube 225, so as to ensure the electric heat wire 221 enough space for performing atomization in the atomizing chamber 227.

The liquid-guide piece 23 is used for leading tobacco liquid from the tobacco-liquid cup 3 to the atomizing cup 22. The liquid-guide piece 23 is made from cotton or fiber, is inserted and fixed in the duct 2261 of the cup cover 226, and has one end thereof extending in the tobacco-liquid cup 3 and the other end extending in the atomizing cup 22, namely in the atomizing chamber 227. The liquid-guide piece 23 is shaped about a long strip with both ends respectively as an absorption end 231 and an effusion end 232. The absorption end 231 is shaped as a column. The effusion end 232 as a cone has outer diameters thereof gradually increased, and shaped as a speaker. In work, the liquid-guide piece 23 absorbs tobacco liquid with its absorption end 231 inserted in the tobacco-liquid cup 3. The effusion end 232 extends into the atomizing chamber 227 with bottom surface thereof abutting against both top surfaces of the liquid-storage member 223 and the liquid-soakage member 224, and tobacco liquid in the liquid-storage member 223 penetrates the liquid-soakage member 224 and further penetrates and is absorbed by the fiber piece 212. The liquid-guide piece 23 facilitates assembly of the inhaling shell 90, and achieves good results of guiding tobacco liquid.

The fiber piece 212 is mounted in the atomizing chamber 227 by virtue of the fix opening 2251 of the support tube 225, such assembly way is very convenient. The electric heat wire 211 winds around the fiber piece 212 with preset positive and negative terminals, the electric heat wire 211 has the positive terminal bent and then tightly fitted between an inner wall of the air hole 2213 of the atomizing cup 22 and an outer wall of the electrode member 14 so as to electrically connect with the electrode member 14 since the electrode member 14 is tightly fitted in the cup seat 221; and the electric heat wire 211 has its negative terminal bent and then fitted between an inner wall of the cup cylinder 222 and the outer wall sidewall 2218 of the cup seat 221 so as to be electrically connected with the mounting sleeve 13 since the cup cylinder 222 is tightly fitted on the cup seat 221. Such tight-fit manner for electrical connection avoids soldering, thus simplifies the process and facilitates the assembly.

In accordance with this embodiment, the atomizing device 2 is held in the mounting sleeve 13, is disposed in the inhaling tube 1 in virtue of the mounting sleeve 13, and has all parts thereof assembled via snap-fit means, which facilitate assembly. When it is necessary to maintain or replace the atomizing device 2, just remove the joint member 5 and take out the atomizing device 2 for independently replacing each part thereof. Disassembly and assembly, maintenance, and replacement thereof are very convenient.

The tobacco-liquid cup 3 (referring to FIGS. 3-4, 11) used for storing tobacco liquid, comprises a cup body 31, a cup base 32, a tobacco-liquid input port 33, a tobacco-liquid output port 34 and a vent groove 35. The cup body 31 is a hollow shell with both ends open, has its top open end defining the tobacco-liquid input port 33, and its diameter are gradually reduced towards the tobacco-liquid input port 33, namely, the cup body 31 has a taper degree adapted to the thermal insulation jacket 12. It may be made from transparent or semi-transparent materials. The cup base 32 covers the bottom open end of the cup body 31. An outer wall of the cup base 32 forms some sealing rings 321, and thus the cup base 32 is tightly fitted in and seals a bottom inner wall of the cup body 31 via the sealing rings 321. The cup base 32 therein defines the tobacco-liquid output port 34 for leading out tobacco liquid, which is disposed at one end of the tobacco-liquid cup 3 being engaged with the liquid-guide piece 23. The duct 2261 of the cup cover 226 is tightly fitted in the tobacco-liquid output port 34, so that the liquid-guide piece 23 seals the tobacco-liquid output port 34 and has its absorption end 231 inserted in the tobacco-liquid cup 3. The vent groove 35 is used for air flowing and is set along the outer wall of the tobacco-liquid cup 3. In this embodiment, the vent groove 35 is disposed in the outer wall of the tobacco-liquid cup 3 and is depressed inwards for forming circular recess, so that after the tobacco-liquid cup 3 is inserted in the thermal insulation jacket 12, a gap is formed between the outer wall of the tobacco-liquid cup 3 and the thermal insulation jacket 12 for air flowing. The vent groove 35 has one end thereof communicated with the air outlet 2262 of the cup cover 226, and has the other end thereof communicated with the environment via an airflow hole in the mouthpiece 4. In assembly, the tobacco-liquid cup 3 is inserted in the thermal insulation jacket 12, the top end of the tobacco-liquid cup 3 abuts against keeps close to the second circular lip 123 of the thermal insulation jacket 12, the bottom end of the tobacco-liquid cup 3 abuts against the top end of the mounting sleeve 13 so that the tobacco-liquid cup 3 is mounted in the thermal insulation jacket 12.

The mouthpiece 4 (referring to FIG. 12) comprises a main body 41 about cylinder-shaped, and a plug 44 adapted to the tobacco-liquid input port 33 of the tobacco-liquid cup 3. The main body 41 therein defines an axial hole 42, and radially defines a radial hole 43; the axial hole 42 has one end thereof communicating air outside of the mouthpiece 4, and the other end communicating the radial hole 43. The plug 44 is disposed at one end of the main body 41 which is engaged with the inhaling tube 1, is made from elastic materials, and is removably inserted in the tobacco-liquid input port 33 of the tobacco-liquid cup 3 so as to seal the tobacco-liquid cup 3; and a sealing gasket 45 is disposed where the plug 44 and the tobacco-liquid input port 33 are engaged. When tobacco liquid in the tobacco-liquid cup 3 is exhausted and necessary to be added again, just remove the mouthpiece 4 from the inhaling tube 1, and add new tobacco liquid into the tobacco-liquid cup 3 from the tobacco-liquid input port 33. Tobacco liquid can be repeatedly added, which is convenient for use.

The joint member 5 used for connecting the inhaling shell 90 with the power shell 91 of the electronic cigarette, is made from metal, and is a hollow shell. The joint member 5 supports the atomizing device 2 in the receiving chamber 135 of the mounting sleeve 13 and is electrically connected with the mounting sleeve 13, and further electrically connected with a second electrode of the electronic cigarette's power supply. A first electrode piece 51 and a first insulation ring 52 are set inside the joint member 5, the first electrode piece 51 is mounted in and electrically isolated from the joint member 5 via the first insulation ring 52; the first electrode piece 51 is electrically connected with a first electrode of the electronic cigarette's power supply; the joint member 5 at its bottom side wall radially defines an air vent 53 so that air of the environment can enter inside of the inhaling shell 90 of the electronic cigarette through the air vent 53.

The inhaling shell 90 further comprises a decoration sheath 6. The decoration sheath 6 is used for decoration or bearing a logo on the inhaling shell 90 of the electronic cigarette, and can be fitted on the outer wall of the mouthpiece 4, so that the inhaling shell 90 of the electronic cigarette is more attractive.

After the inhaling shell 90 is assembled, the air inlet 131 of the mounting sleeve 13, the air vent 53 and a center through hole of the joint member 5, the venthole 141 of the electrode member 14, the air hole 2213 of the atomizing cup 22, the atomizing chamber 227 of the atomizing device 2, the air outlet 2262 of the atomizing cup 22, the vent groove 35 in the outer wall of the tobacco-liquid cup 3, and the radial hole 43 and the axial hole 42 of the mouthpiece 4, are successively communicated and connected to form the air-puffing passage 7 of the present invention; air and aerosol generated from vaporization of tobacco liquid flow through the air-puffing passage 7 and enter smoker's mouth. Such configuration of the air-puffing passage 7 make unnecessary to specially design or preset a space in the inhaling tube 1 for the air-puffing passage 7, so that the structure of the inhaling tube 1 is more compact.

The power shell 91 therein is set with a power supply 911, a second electrode 912 and an insulating ring 913. The second electrode 912 is mounted in the power shell 91 and is electrically isolated from the other electrode of the power shell 91 by the insulation ring 913, and abuts against the first electrode piece 51 inside the joint member 5 so as to electrically connect with the electrode member 14. An outer wall of the power shell 91 is further set with a power switch 914, and the electronic cigarette is controlled on and off by the power switch 914. If the power switch 914 is pressed, an electric circuit is connected, then a direction of current is as: from a positive electrode of the power supply 911 in the power shell 91 to the second electrode 912, through the first electrode piece 51 inside the joint member 5 to the electrode member 14, entering the positive terminal of the electric heat wire 211, through the negative terminal of the electric heat wire 211 to the cup cylinder 222 of the atomizing cup 22, through the cup cover 226 to the mounting sleeve 13, then through the outer wall of the joint member 5 back to a negative electrode the power supply 911 in the power shell 91.

The above description discloses the specific embodiments of the present invention. Note that those skilled in the art will appreciate multiple modifications and variations in light of the features of the present invention, and those modifications and variations shall be deemed within the scope of this invention.

What is claimed is:

1. An inhaling shell of an electronic cigarette, comprising:
a mouthpiece defining an airflow hole therein and with a sealing plug extending at one end thereof;
an inhaling tube with a top open end and a bottom open end;
a tobacco-liquid cup with one end open for forming a tobacco-liquid output port and the other end open for forming a tobacco-liquid input port;
tobacco liquid stored in the tobacco-liquid cup; and
an atomizing device;
wherein the end of the mouthpiece with the sealing plug is inserted in the top open end of the inhaling tube, the tobacco-liquid cup is fitted in the inhaling tube with the tobacco-liquid input port aligned to and behind the top open end of the inhaling tube, an outer wall of the tobacco-liquid cup is located inside an inner wall of the inhaling tube, a gap is formed between the outer wall of the tobacco-liquid cup and the inner wall of the inhaling tube for air flowing and communicated with the airflow hole in the mouthpiece; the mouthpiece seals the tobacco-liquid input port with the sealing plug being inserted and tightly fitted in the tobacco-liquid input port; and the atomizing device is provided in the inhaling tube behind the tobacco-liquid output port of the tobacco-liquid cup; said atomizing device comprises an atomizing cup and an atomizer; said atomizing cup therein defines an atomizing chamber for receiving the atomizer and communicated with the gap; said atomizer comprises an electric heat wire and a fiber piece for supporting the electric heat wire and absorbing tobacco liquid; said atomizing cup comprises a cup seat, a cup cover, and a cup cylinder with its lower end fitted on the cup seat; the cup cover fits on an upper end of the cup cylinder opposite to the cup seat and is tightly fitted in the tobacco-liquid output port; a liquid-guide piece is inserted through the cup cover and guides tobacco liquid from the tobacco-liquid cup to the atomizer inside of the atomizing cup is further set with a support tube mounted on the cup seat and a liquid-storage member fitted around outside of the support tube; said fiber piece is fixed on the support tube, and both ends of the fiber piece abut against an inner wall of the liquid-storage member and absorb tobacco liquid for vaporization.

2. The inhaling shell according to claim 1, wherein said cup cover is set with a duct thereon of which an outside wall is tightly fitted in the tobacco-liquid output port of the tobacco-liquid cup; the liquid-guide piece is inserted through the duct; the liquid-guide piece has one end thereof extending into said tobacco-liquid cup and has the other end extending into said atomizing cup and abutting against said liquid-storage member so as to guide tobacco liquid from the tobacco-liquid cup into the atomizing cup.

3. The inhaling shell according to claim 2, wherein the sealing plug of said mouthpiece adapted to said tobacco-liquid input port; said sealing plug removably seals said tobacco-liquid input port so as to add tobacco liquid repeatedly; the cup seat comprises a circular bottom, a sidewall, and a periphery of the bottom forms a cup flange, a groove is defined between the cup flange and the sidewall for fixing the cup cylinder, the cup seat therein is further set with a positioning column for locating the support tube, and the positioning column axially and upwards extends from the circular bottom; the atomizing chamber as a hollow cavity is defined by the cup seat, the cup cylinder, and the cup cover together; the fiber piece of the atomizer is axially positioned in the atomizing chamber by virtue of the liquid-storage member, and is radially positioned by virtue of both the liquid-guide piece and the support tube.

4. The inhaling shell according to claim 1, wherein the outer wall of the tobacco-liquid cup defines a vent groove set therealong to form the gap between the outer wall of the tobacco-liquid cup and the inhaling tube for air flowing; the cup seat defines an air hole therethrough and communicated with the atomizing chamber; an air outlet is defined in the cup cover and communicates the atomizing chamber to the vent groove; the air hole, the atomizing chamber, the air outlet, and the vent groove along the outer wall of the tobacco-liquid cup with one end thereof communicated with the air outlet of the cup cover and the other end communicated with environment via the airflow hole in the mouthpiece, together form an air-puffing passage for vapor of tobacco liquid from the atomizer flowing therethrough to the mouthpiece for user smoking.

5. The inhaling shell according to claim 1, wherein said inhaling tube therein is further set with a thermal insulation jacket for heat insulation, the thermal insulation jacket is disposed between an inner wall of the inhaling tube and the tobacco-liquid cup, and the tobacco-liquid cup and the atomizing device are received in the thermal insulation jacket.

6. The inhaling shell according to claim 4, wherein the inhaling tube therein is further set with a mounting sleeve for mounting the tobacco-liquid cup and receiving the atomizing device; and the mounting sleeve abuts against the cup cover and both are electrically connected.

7. The inhaling shell according to claim 6, wherein an electrode member of the atomizing device is inserted in the cup seat in the air hole of the atomizing cup; the electrode member is shaped as a cylinder, defines a venthole axially running through center of the electrode member and communicated with the air hole of the cup seat; the electric heat wire has one end thereof tightly fitted on an outer wall of the electrode member for electric connection, and has the other end tightly fitted on an inner wall of the cup cylinder for electric connection; and the cup cylinder and the cup cover are electrically connected.

8. The inhaling shell according to claim 7, wherein the bottom open end of the inhaling tube opposite to the mouthpiece is installed with a joint member for mounting the atomizing device in the mounting sleeve, the joint member and the mounting sleeve are moveably engaged and electrically connected with each other; an electrode piece with a center through-hole therein is fixed in the joint member via an insulating ring, and electrically contacts an end of the electrode member of the atomizing device which is inserted in the cup seat, while the center through-hole of the electrode piece communicates the air hole of the atomizing cup; and the joint member in a sidewall thereof defines an air vent communicating said center through-hole.

9. The inhaling shell according to claim 4, wherein the cup cylinder, the liquid-storage member, and the support tube are shaped about as a cylinder and coaxially arranged; the liquid-storage member in an inner wall thereof is further installed with a liquid-soakage member which has a cylindrical shape and a high-temperature resistance, the liquid-soakage member is fitted on outside of the support tube; both ends of the fiber piece abut against an inner wall of the liquid-soakage member; tobacco liquid into the atomizing chamber from the liquid-guide piece is absorbed and stored in the liquid-storage member, penetrates the liquid-soakage member, and is sucked into the fiber piece for atomization; the support tube at a top end thereof defines fix openings which radially penetrate through a wall of the support tube and are used for supporting the fiber piece; inside of the cup seat is further set with a positioning column for locating the support tube, the positioning column axially projects upwards to a certain height from a bottom center of the cup seat; the air hole of the atomizing cup axially runs through the positioning column and the bottom of the cup seat; and the bottom of the cup seat further defines a wire-through hole for the electric heat wire passing therethrough.

10. The inhaling shell according to claim 9, wherein the liquid-storage member is made from liquid-absorbing cotton or fiber; the liquid-soakage member is made from high-temperature resistant cotton or fiber; and the support tube is made from glass fiber.

11. The inhaling shell according to claim 1, wherein the liquid-guide piece is a kind of cotton or fiber which can absorb tobacco liquid, the liquid-guide piece is shaped about a long strip with both ends respectively as an absorption end and an effusion end, the absorption end is shaped as a column, the effusion end as a cone has outer diameters thereof gradually increased; the liquid-guide piece absorbs tobacco liquid with its absorption end inserted in the tobacco-liquid cup; the effusion end extends into the atomizing chamber with a bottom surface thereof contacting with a top surface of the liquid-storage member.

12. The inhaling shell according to claim 1, wherein the mouthpiece is shaped about as a cylinder, the sealing plug is made from elastic materials; a sealing gasket is disposed where the sealing plug and the tobacco-liquid input port are engaged; and the airflow hole comprises an axial hole intercommunicated with a radial hole; the axial hole has one end thereof communicating air outside of the mouthpiece, and the other end communicating the radial hole; the radial hole is communicated with the gap for air flowing; and the radial hole is defined radially through an wall of the cylinder and located above the sealing plug.

13. The inhaling shell according to claim 1, wherein the inhaling tube is a tapered cylinder with decrescent diameter.

14. The inhaling shell according to claim 1, wherein the inhaling tube is set with an observation window for observing tobacco-liquid volume in the tobacco-liquid cup, the tobacco-liquid cup is wholly or partly transparent; and the inhaling tube is fitted with a decoration sheath for decoration or bearing a logo.

15. An electronic cigarette comprising the inhaling shell according to claim 1, and a power shell connecting with the inhaling shell.

16. The electronic cigarette according to claim 15, wherein said inhaling tube therein is further set with a thermal insulation jacket for heat insulation, the thermal insulation jacket is disposed between an inner wall of the inhaling tube and the tobacco-liquid cup; and the tobacco-liquid cup and the atomizing device are received in the thermal insulation jacket.

17. The electronic cigarette according to claim 15, wherein the air hole and the atomizing chamber of the atomizing cup, an air outlet defined in the cup cover communicated with the atomizing chamber, and a vent groove defined in an outer wall of the tobacco-liquid cup with one end thereof communicated with the air outlet of the cup cover and the other end communicated with an airflow hole defined in the mouthpiece, together form an air-puffing passage for air and vapor generated from atomization of tobacco liquid by the atomizer to flow therethrough to the mouthpiece for user smoking.

18. An inhaling shell of an electronic cigarette, comprising:
a mouthpiece defined an airflow hole therein and with a sealing plug extending at one end thereof;
an inhaling tube with an open top end and a bottom open end;
a tobacco-liquid cup with a tobacco-liquid output port and a tobacco-liquid input port;
tobacco liquid is stored in the tobacco-liquid cup; and
an atomizing device;
wherein the end of the mouthpiece with the sealing plug is removably inserted in the top open end of the inhaling tube, the tobacco-liquid cup is inserted in the inhaling tube with the tobacco-liquid input port aligned to and behind the open top end of the inhaling tube, an outer wall of the tobacco-liquid cup is located inside an inner wall of the inhaling tube, a vent groove is formed between the outer wall of the tobacco-liquid cup and the inner wall of the inhaling tube for air flowing and communicated with the airflow hole in the mouthpiece; the mouthpiece seals the tobacco-liquid input port with the sealing plug being inserted and tightly fitted in the tobacco-liquid input port; and the atomizing device is provided in the inhaling tube behind the tobacco-liquid output port of the tobacco-liquid cup.

19. The inhaling shell according to claim 18, wherein said atomizing device comprises an atomizing cup and an atomizer; said atomizing cup comprises a cup seat, a cup cover, and a cup cylinder with a lower end being fitted on the cup seat and an upper end thereof being covered by the cup cover; an atomizing chamber is defined by the cup seat, the cup cylinder and the cup cover together, said atomizing cup therein defines an atomizing chamber for receiving the atomizer.

20. The inhaling shell according to claim 19, wherein the outer wall of the tobacco-liquid cup defines the vent groove along; the cup seat defines an air hole therethrough and communicated with the atomizing chamber; an air outlet is defined in the cup cover and communicates the atomizing chamber to the vent groove; the air hole, the atomizing chamber, the air outlet, and the vent groove along the outer wall of the tobacco-liquid cup with one end thereof communicated with the air outlet of the cup cover and the other end communicated with environment via the airflow hole in the mouthpiece, together form an air-puffing passage for vapor of tobacco liquid from the atomizer flowing therethrough to the mouthpiece for user smoking.

* * * * *